United States Patent [19]

De Frank et al.

[11] 4,227,527

[45] Oct. 14, 1980

[54] STERILE AIR VENT

[75] Inventors: Michael P. De Frank, Woodstock; James W. Scott, Lindenhurst, both of Ill.

[73] Assignee: Baxter Travenol Laboratories, Inc., Deerfield, Ill.

[21] Appl. No.: 953,576

[22] Filed: Oct. 23, 1978

[51] Int. Cl.³ .................. A61M 5/00; B01D 39/06
[52] U.S. Cl. .................. 128/214 R; 128/214 C; 55/279; 55/385 C; 55/523
[58] Field of Search .............. 55/279, 385 C, 523, 55/527, 528, 529; 422/291; 128/214 R, 214 C, 214.2, 349 R; 428/523; 206/63.3; 220/371; 210/510

[56] References Cited

U.S. PATENT DOCUMENTS

| | | | |
|---|---|---|---|
| 2,297,817 | 10/1942 | Truxell, Jr. et al. | 55/529 |
| 2,604,958 | 7/1952 | Leufvenius | 55/523 |
| 2,816,545 | 12/1957 | Jacoby | 128/214.2 |
| 2,972,991 | 2/1961 | Burke | 128/218 |
| 2,982,418 | 5/1961 | Bailey | 210/448 |
| 3,008,570 | 11/1961 | Roehr et al. | 206/43 |
| 3,048,537 | 8/1962 | Pall et al. | 210/510 |
| 3,121,685 | 2/1964 | Hazell | 210/446 |
| 3,193,993 | 7/1965 | Barton et al. | 55/527 |
| 3,306,291 | 2/1967 | Burke | 128/218 |
| 3,322,114 | 5/1967 | Portnoy et al. | 128/2 |
| 3,606,001 | 9/1971 | Talonn et al. | 206/63.2 |
| 3,662,752 | 5/1972 | Yokoyama | 128/214 R |
| 3,744,640 | 7/1973 | Grover | 210/463 |
| 3,753,500 | 8/1973 | Voegeli | 210/510 |
| 3,817,389 | 6/1974 | Weichselbaum | 210/448 |
| 3,865,731 | 2/1975 | Seitz | 210/359 |
| 3,868,973 | 3/1975 | Bierman et al. | 138/43 |
| 3,882,026 | 5/1975 | McPhee | 210/510 |
| 3,933,652 | 1/1976 | Weichselbaum | 210/510 |
| 3,969,250 | 7/1976 | Farr | 210/359 |
| 3,976,259 | 8/1976 | Weichselbaum | 210/510 |
| 3,981,297 | 9/1976 | Dunn et al. | 128/214 R |
| 4,084,949 | 4/1978 | Biggins | 55/527 |
| 4,095,810 | 6/1978 | Kolle | 277/208 |
| 4,106,509 | 8/1978 | McWhorter | 128/349 B |
| 4,193,399 | 3/1980 | Robinson | 55/523 |

FOREIGN PATENT DOCUMENTS 586809 12/1958 Italy ..................... 128/214 C

OTHER PUBLICATIONS

Reinsch, Earl; Filters Made of Porous Metal can be Fabricated in Special Shapes, Nov. 1944, Product Eng., pp. 769-771.

Primary Examiner—David L. Lacey
Attorney, Agent, or Firm—Paul C. Flattery; John P. Kirby, Jr.; Gary W. McFarron

[57] ABSTRACT

A sterile air vent is disclosed which permits the passage of gas but is substantially impervious to microorganisms. The vent may be used on a variety of medical apparatus and it is particularly suitable as a tip protector for the tip ends of medical fluid administration sets or the like. The filtering is provided by a solid micro-porous plug of selected material carried in an air passageway of the vent housing, which housing is adapted for attachment to the desired medical apparatus. The plug is sufficiently porous to permit gas to pass through while filtering out bacteria or other organisms which would impair the sterility of the medical apparatus.

4 Claims, 3 Drawing Figures

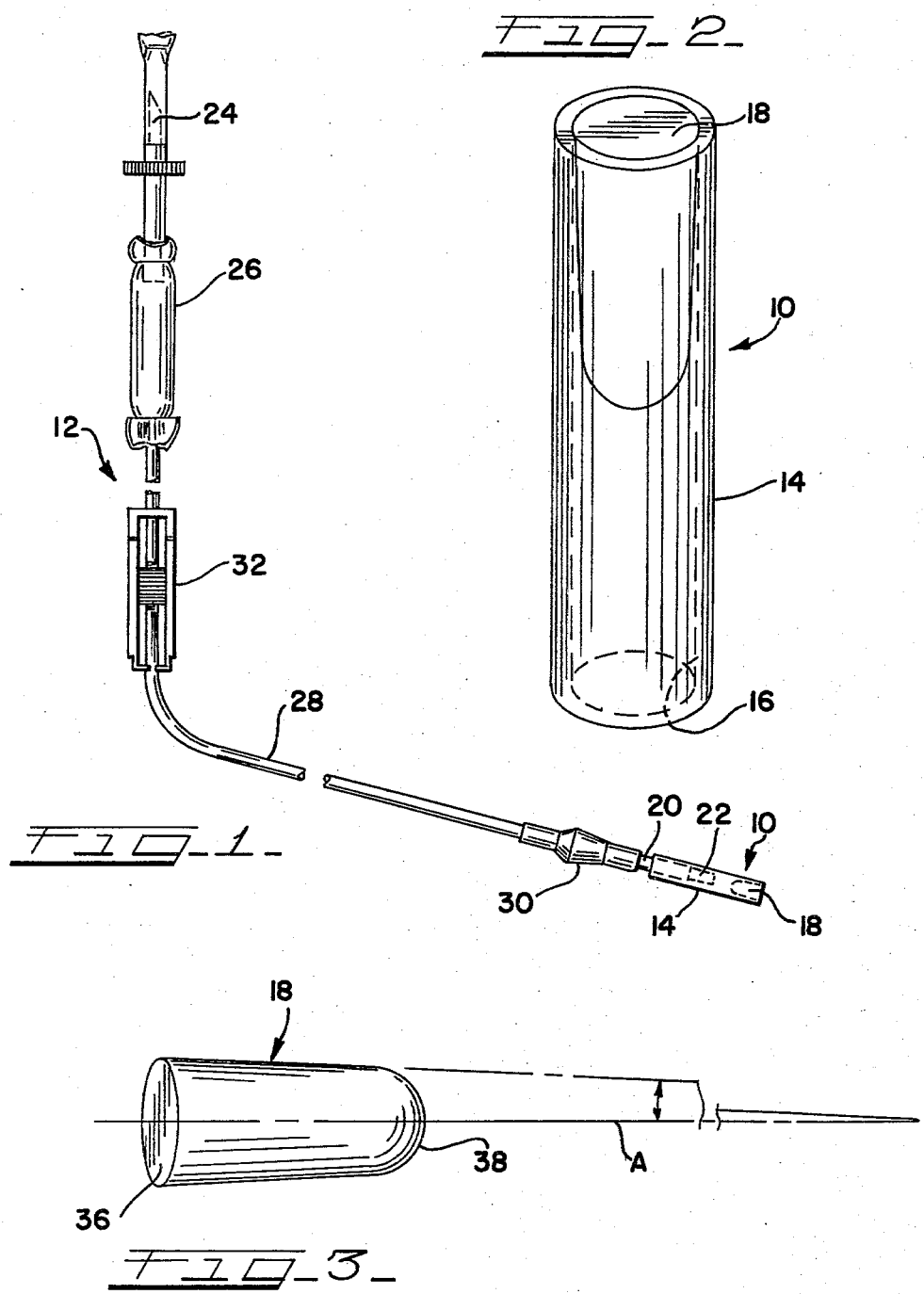

STERILE AIR VENT

The present invention relates generally to air vents and, more particularly, to sterile air vents which may be attached to medical apparatus to permit venting while at the same time preventing contamination of the apparatus by bacteria or other microorganisms.

Sterile air vents are used in a wide variety of applications in the medical field. For example, they are often employed with glass intravenous solution containers or the like which require venting for proper operation. One such vent is shown in U.S. Pat. No. 3,157,481 to Bujan. The vent there may be used with a piercing needle or as a vent cap to vent displacement air into the IV container. A water-repellent, micro-porous filter membrane in the vent prevents leakage and filters out bacteria while permitting air to vent into the container.

Sterile air vents may also be used in connection with medical equipment to maintain the equipment sterile until it is ready for use. Typically, medical apparatus, such as intravenous fluid or blood administration sets employ tip protectors which cover and seal the tubular hubs, needle-receiving luers, spikes or the like provided at the ends of the set. These protectors maintain the inside of the set as well as a portion of the surface of the tip in sterile condition until it is ready for opening and use with a patient. Often, tip protectors are closed plastic tubes which telescope over and seal the tip end of the particular administration set or the like. One example of this type of tip protector is shown in U.S. Pat. No. 4,095,810 to Kulle.

Although sealed plastic tip protectors adequately protect the sterility of administration sets, it is sometimes desirable for the tip protector to permit air or gas to vent into the inside of the administration set or medical apparatus while preventing the passage of microorganisms. For example, such a protector permits the use of a sterilizing gas such as ethylene oxide, to sterilize the set after it has been completely assembled and keeps it sterile until it is ready for use. In addition to the vent cap described above in U.S. Pat. No. 3,157,481, venting tip protectors have also been made from plastic tubing with a cotton wadding which is sufficiently porous to permit gas to pass through, but provides a satisfactory barrier to microorganisms. However, the membrane type tip protector requires relatively complex assembly equipment and techniques, and the cotton-filled tip protector is extremely difficult to automate, and is substantially a manual operation.

Accordingly, it is a general object of the present invention to provide an improved sterile air vent which is easy to manufacture and of relatively low cost.

It is a further object of the present invention to provide a sterile air vent which may be employed as a tip protector for medical fluid administration sets.

These and other objects of the present invention are shown in the following detailed description and the attached drawings, of which, FIG. 1 is an elevational view of a typical medical fluid administration set employing a sterile air vent made in accordance with the present invention as a tip protector;

FIG. 2 is a perspective view of a sterile air vent employing the present invention; and FIG. 3 is a perspective view of a solid micro-porous plug used in the air vent of FIG. 2.

The present invention is generally embodied in a versatile sterile air vent 10 adapted for attachment to medical apparatus either as a simple air vent or as a tip protector for an intravenous fluid or blood administration set, such as that shown generally at 12. In accordance with the present invention, the vent includes a housing 14 with an internal air passageway 16. A unique solid, plastic micro-porous plug 18 is positioned within the air passageway to permit the passage of air or other gaseous material therethrough while filtering out microorganisms which would destroy the sterility of the medical apparatus.

By employing a vent housing 14 of tubular form, as shown in the drawings, the sterile air vent 10 is particularly suitable for sealing a tip 20 of the medical fluid administration set 12. Depending on the desired application, the tip end may be a spike, a needle adapter, a tubular hub, a needle-receiving luer, or the like, and the present invention may be employed with any of these. In the illustrated embodiment, the tip 20 is a needle adapter, with a tapered needle-receiving luer 22 which is telescoped into the tubular vent housing 14, and surface-to-surface frictional contact between the vent housing and the tip seals the set against contamination. The solid, plastic porous plug 18 is positioned in the other end of the tubular vent housing and serves to filter out bacteria while permitting gas, such as ethylene oxide, to enter the interior of the set to sterilize it. After sterilization, the micro-porous plug maintains the interior of the set as well as the enclosed surface of the tip in sterilized condition until the air vent 10 is removed when the set is ready for use.

Turning now to a more detailed description of the preferred embodiment of the present invention, the versatile sterile air vent 10 may be employed as an air vent for medical apparatus which require venting, e.g., glass IV containers, but the preferred embodiment of the present invention is particularly useful as a tip protector for intravenous fluid administration sets and the like. For example, in FIG. 1, a typical intravenous fluid administration set is illustrated. A spike 24 is provided at the upper end of the set for insertion into a reservoir of parenteral fluid, blood or similar fluid (not shown). The fluid drains by gravity through the spike and into a drip chamber 26, which permits medical personnel to determine the flow rate of the fluid by counting the number of falling drops in a given period of time. From the drip chamber, the fluid flows through a long plastic tube 28 which terminates with a plastic needle-adapter tip 20 which has a tapered end portion 22, often called a luer connector. The tapered end is of a standard size and is used to provide a telescoping frictional fit with a needle housing or the like for administering the medical fluid to a patient. A blood flashback indicator 30 may also be used between the tubing and the tip 20 for identifying when the needle has entered the patient's vein, and a roller clamp 32 may be used to control the flow of fluid through the administration set.

Of course, the current practice is to provide the administration set 12 as a one-time use item, pre-sterilized and ready for immediate use by the physician or nurse. Accordingly, it is necessary that the set be sterilized after it is manufactured and maintained in a sterile condition until it is used. In particular, it is important that the open ends of the set be sealed so that microorganisms cannot enter the set, and so that those outside surface areas of the tip ends which come into contact with the medical fluid or with the devices for administering the fluid are also maintained sterile. For example, with luer connectors, the surface of the tapered end telescopes inside a needle housing or other connecting member and, therefore, must be maintained sterile. In FIG. 1, a typical tip protector 34 is shown telescoped over the spike 24. This protector is a piece of plastic tubing, heat-sealed at one end to completely prevent air or bacteria from entering and opening at the other end. It is appropriately sized for a tight fitting sealed engagement over the spike 24.

The sterile air vent 10 made in accordance with the present invention is shown fitted over the tapered outlet end of the administration set. This vent permits sterilizing gas to enter the set while maintaining the surface of the tip end sterile and preventing microorganisms from contaminating the set.

As seen more clearly in FIG. 2, in the illustrated embodiment of the air vent 10, the vent housing 14 is an elongated plastic tube, generally cylindrical in shape with the internal bore or passageway 16 of the tube extending between the ends thereof. Although the vent housing of the present invention may be of a variety of sizes and shapes, the elongated, plastic tubular housing offers a significant simplicity when the present invention is employed as a tip protector. The tube may be made from a variety of materials, but it is preferably constructed of resilient plastic, such as ethylene vinyl acetate (EVA), which is of low cost and sufficiently elastic to help hold the porous plug 18 in place. Resilient plastic also permits a tight compressive fit over the tip end 20 without danger of splitting or cracking that occurs in some semi-rigid materials.

To permit gas or air to pass through the passageway 16 but to prevent the passage of microorganisms, the solid porous plug 18 is press fit into the passageway 16 of the resilient tube 14. A solid but porous plug makes assembly of the air vent relatively simple and permits automation which further reduces cost. It does not require the relatively complex or manual assembly required by the membrane and cotton air vents discussed earlier, and yet it does provide a positive barrier to bacteria.

Preferably, the plug 18 is of plastic material, and one material which has been found to be particularly advantageous is a sintered micro-porous polyethylene available under the trademark "POREX" from Glasrock Products, Inc. of Atlanta, Georgia. This particular material has been employed as a reagent filter in U.S. Pat. No. 3,774,640, and it has also been used with intravenous catheter units for permitting air to escape from blood flashback chambers. However, neither of these are directed to the use of solid porous plastic materials as primary sterile barriers of the type described in this application, and neither detract from the significance of the present invention as an especially unique sterile air vent, and particularly as a new and improved tip protector for medical fluid administration sets.

The particular size of the tubular vent housing 14 and the porous plug 18 are variable, depending on the particular application. The tubular housing should have an inside diameter sufficiently small for a tight frictional fit over the tip of the set, whether the tip be a spike, needle adapter or the like and the plug should be of sufficiently large diameter for a tight frictional fit within the tube. For example, with a fluid administration set having a needle adapter tip 20 which tapers at about a 1 degree angle to a diameter of about 0.210 inches adjacent the luer connector 22, it has been found that the plastic tubular housing 14 preferably has an inside diameter of about 0.208 inches plus or minus 0.003 inches, a wall thickness of about 0.020–0.040 inches and may have a length of from 1 to 2 inches. These dimensions are for a vent housing constructed of ethylene vinyl acetate, such as that available from DuPont under the trademark "ALATHON 3130". Plastic having higher or lower percentages of vinyl acetate may need thicker or thinner walls, respectfully. In any event, with the preferred material and the dimensions selected above, the open end of the tube fits tightly about the tip 20 of the fluid administration set and seals the set against the entry of air or microorganisms.

The dimensions of porous plug 18 provided in the other end of the vent housing 14 may also be varied, depending on the dimensions of the tubular housing 14 and, in addition, on the degree of filtration required. For example, the diameter of the plug should be slightly larger than the bore 16 of the tube for a tight compressive fit, and the length of the plug may be varied to provide for finer or coarser filtration—the longer the plug, the longer the filtration path and thus, the finer the filtration. In accordance with the present invention, referring particularly to FIG. 3, the plastic vent plug is generally cylindrical, but tapers slightly from a flat base 36 to a rounded end 38 for ease of insertion. To provide a tight, wedge fit within the tubular housing described above the preferred micro-porous plug has a base end diameter of approximately 0.246 inches and a rounded end diameter of about 0.210 inches, both of which are larger than the inside diameter of the tube 14. The plug may have a pore size of from 10 to 20 microns, with the length varying from about 0.25 inches to 0.50 inches depending on the degree of filtration required. Preferably, a plug with a 10 micron pore size is employed, having a length of about 0.425 inches.

Insertion of the plug into the tube 14 is facilitated by the rounded end 38, which is curved at a radius of about 0.105 inches, and the taper from the base end to the rounded end. With the base end diameter and the length set forth above, the plug 18 has a taper of about 4° relative to the central axis A of the plug, although a taper from 1°–5° would probably be satisfactory.

In accordance with the invention described above, a unique sterile air vent is provided which is not only versatile, but is extremely easy to assemble, and may be assembled automatically at a great reduction in cost. The resilient housing of the preferred embodiment permits its use on various devices, with widely differing dimensions and tolerances. The novel filtering element is unique in this application and permits gas to pass through while effectively sealing out bacteria and microorganisms. It does not have the complexity of a membrane seal and provides a positive barrier to bacteria.

Although the present invention is described in terms of the preferred embodiment, this application is intended to include those equivalent structures which may be obvious to one skilled in the art after reviewing this application.

What is claimed is:

1. A sterility preserving tip protector for overfitting one end of a medical fluid administration set and the like comprising:

an elongated resilient plastic tube;
a unitary microporous sintered plastic filter element in the shape of a plug received within one end of said tube, the other end of said tube being open for fitting over one end of the administration set, said filter element having a pore size of between 10 and 20 microns inclusive, and a length of between 0.25 and 0.5 inches inclusive, to preserve sterility of the set and to readily pass gas therethrough.

2. A tip protector in accordance with claim 1 wherein said filter element is frictionally retained within said tube.

3. A tip protector in accordance with claim 2 wherein said plug-shaped filter element includes tapered sidewalls, the diameter of one end of said element being larger than the inside diameter of said plastic tube.

4. A tip protector in accordance with claim 1 wherein said plastic filter element is sintered polyethylene.

* * * * *